United States Patent [19]

Horne

[11] Patent Number: 4,519,390
[45] Date of Patent: May 28, 1985

[54] FIBER OPTIC LASER CATHETER

[75] Inventor: Kenneth J. Horne, Kaysville, Utah

[73] Assignee: HGM, Inc., Salt Lake City, Utah

[21] Appl. No.: 438,041

[22] Filed: Oct. 15, 1982

[51] Int. Cl.³ .......................... A61N 5/06; A61B 17/36
[52] U.S. Cl. .................................. 128/303.1; 128/395
[58] Field of Search ..................... 128/303.1, 395–398; 372/6, 108; 219/121 L, 121 LP

[56] References Cited

U.S. PATENT DOCUMENTS

| | | | |
|---|---|---|---|
| 3,466,566 | 9/1969 | Patel | 372/108 X |
| 3,821,510 | 6/1974 | Muncheryan | 128/303.1 X |
| 4,273,109 | 6/1981 | Enderby | 128/303.1 X |

FOREIGN PATENT DOCUMENTS

| | | | |
|---|---|---|---|
| 2656278 | 6/1978 | Fed. Rep. of Germany | 128/303.1 |
| 2479485 | 10/1981 | France | 128/303.1 |
| 2076993 | 12/1981 | United Kingdom | 128/303.1 |

Primary Examiner—Edward M. Coven
Attorney, Agent, or Firm—B. B. Olive

[57] ABSTRACT

The present invention is directed to a novel laser catheter assembly including a unitary connector for coupling a laser beam in proper alignment with an optical fiber. An optical fiber assembly comprising an optical fiber interposed within a catheter tube is permanently mounted to the connector which is of one-piece molded construction. A presently preferred embodiment of the connector has an axial bore at the proximal end thereof of substantially the same diameter as the optical fiber, and a second bore larger than the diameter of the fiber, the second bore being in communication with a source of coolant. In a preferred embodiment the connector is further provided with a cavity in the area about the proximal tip of the optical fiber so as to minimize fouling of the fiber tip in the event of misalignment of the laser beam.

1 Claim, 3 Drawing Figures

FIBER OPTIC LASER CATHETER

BACKGROUND

1. The Field of the Invention

The present invention relates to fiber optic catheter assemblies used as a waveguide for carrying laser light energy. More particularly, the present invention is directed to a novel laser catheter assembly utilizing a unitary connector for interconnecting an optical fiber with a laser light source.

2. The Prior Art

Lasers have become increasingly important in surgical applications since the first use of an argon laser in the treatment of diabetic retinopathy in 1965. Success with the argon laser eventually led to research into the possible uses of other commonly available lasers, such as the $CO_2$ and Nd-YAG lasers, each different laser having particular characteristics which make it useful in different surgical settings.

Lasers operate on biological tissues to different degrees depending upon whether the particular laser beam is absorbed, reflected, scattered, or transmitted by the tissue. The primary effect of laser light on biological tissues is thermal energy caused by absorption. Laser beams from different types of lasers are typically absorbed by different tissues in the body. Depending upon the amount of energy in the laser beam, this thermal energy can act to vaporize the tissue, or merely to coagulate it.

With the development of optical fibers, even greater flexibility and increased applications for laser surgery became apparent. This was especially true of the argon laser because of certain very useful properties: it is highly absorbed by melanin and hemoglobin, yet is only weakly absorbed by other body tissues. Further, the argon laser beam may be transmitted through small-diameter optical fibers, allowing great maneuverability and precision during surgery. As a result of these advances, argon lasers are currently used in many applications in plastic surgery, dermatology, neuro-surgery, gastroenterology, urology, bronchoscopy, and otorhinolaryngology. Argon lasers have been shown extremely effective in many situations adaptable to endoscopic surgery and requiring general hemostasis, coagulation of vascular lesions, or coagulation of mucosal lesions.

In the past, it has been thought necessary to utilize very complex connectors for interconnecting the optical fiber with a laser source, these connectors consisting of a number of very carefully machined metal parts adapted to fit together with great precision so as to precisely align the optical fiber with the laser beam. Some of the prior connectors have even incorporated a series of lenses to focus the laser beam onto the end of the optical fiber. Conventional connectors also incorporate a convex gold collar disposed about the end of the optical fiber so as to provide an inert reflective surface for the laser beam in the event it is misdirected away from the end of the optical fiber.

While these prior connectors have proven effective, they are disadvantageous for several reasons. For instance, prior connectors are very expensive to manufacture because of the number of parts that must be carefully produced so as to fit together to extremely close tolerances; even a very slight misfit will result in misalignment of the optical fiber and the laser beam. In addition to the significant expense incurred in machining these parts to such fine tolerances, the expense is compounded due to the fact that when one of these expensive parts does not meet these tolerances, it must be discarded. Further, the cost of materials is quite significant when manufacturing conventional couplers since they are constructed from alloy metal components, and at least one part involves the use of gold.

The disadvantage of the high cost of these conventional connectors is somewhat offset by the fact that they are reusable. Unfortunately, the optical fiber held by these connectors is typically in need of repair or replacement after only a few surgical operations, an operation which requires disassembly of the connector, followed by reassembly of the various connector components together with the new or repaired optical fiber. Because of the need for extremely precise positioning of the optical fiber within the connector it has been necessary heretofore to send the entire laser catheter assembly back to the factory for repair or replacement of the optical fiber. Inasmuch as the turnaround time for these repairs is generally several weeks, it has proven necessary for hospitals performing a large number of laser surgical operations to have a large number of laser catheter assemblies in its inventory. This has required a very large capital outlay and a significant inventory cost, which in turn results in large costs which must be passed on to the patient. Use of these conventional connectors also causes difficulty to hospital administration in allocating costs attributable to capital depreciation, repairs, sterilization, and the like.

Even more significantly, reuse of a laser catheter assembly incorporating a conventional coupler exposes patients to substantial risk. Although in some surgical procedures the laser catheter is merely grasped by the fingers of the physician at a position near the distal end of the catheter and wielded much like a light pen, in many cases it is necessary to actually insert the catheter within a body cavity, usually in connection with an endoscope.

Accordingly, it is of paramount importance to insure that the laser catheter assembly is sterile when it is to be inserted into a surgical site. However, the use of a multiplicity of parts in the conventional connector provides many locations where foreign material can accumulate, thus making it difficult to maintain proper sterility as the connector is used time and again.

This is compounded by the fact that a coolant is typically introduced into the connector and directed along the length of the optical fiber before venting at the working end of the catheter. This coolant often serves as a carrier for bacteria or the like from the connector and to the surgical site.

Additionally, as a conventional connector is disassembled and reassembled over its useful lifetime, small amounts of the material from which the connector is constructed abrade or otherwise break loose from the connector and may be carried into a patient along with coolant.

Thus, it will be appreciated that it would be a significant advancement in the field of laser catheter technology if a simpler and less expensive laser catheter assembly and connector could be provided that would properly position the optical fiber in the path of the laser beam and would reduce the risk caused by the present practice of reusing the laser catheter assembly.

BRIEF SUMMARY AND OBJECTS OF THE INVENTION

The present invention is directed to a novel laser catheter assembly including a unitary connector of molded construction that is readily and inexpensively manufactured to appropriate tolerances, yet effectively couples an optical fiber assembly to a laser light source, the optical fiber assembly being permanently mounted within an interior cavity of the connector such that the entire laser catheter assembly is disposable as a single unit.

It is, therefore, a general object of the present invention to provide an improved unitary laser catheter assembly that is significantly less expensive to manufacture than earlier assemblies.

It is another object of the present invention to provide an improved and inexpensive unitary connector for positioning the receiving end of the optical fiber in the proper orientation with respect to the laser beam that does not require the use of a plurality of carefully machined components.

Yet another object of the invention is to provide a disposable laser catheter assembly.

These and other objects and features of the present invention will become more fully apparent from the following description and appended claims taken in conjunction with the accompanying drawing.

DETAILED DESCRIPTION OF THE INVENTION

Figure 1:
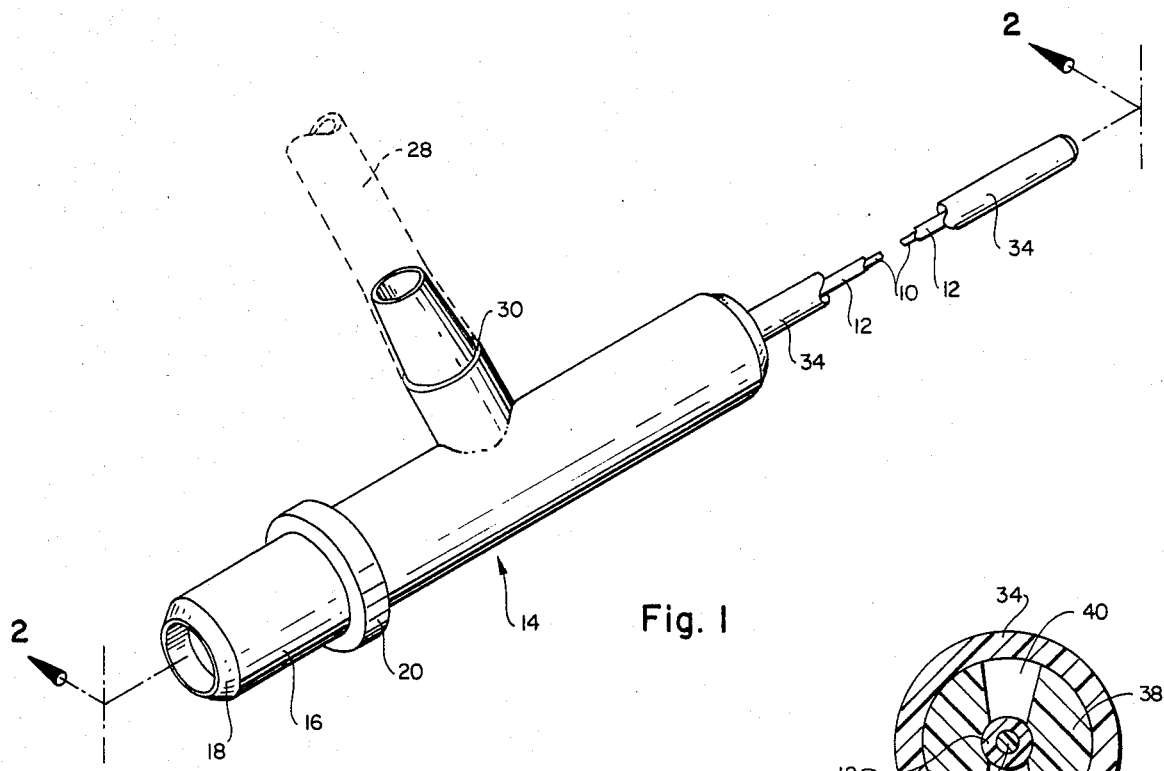
FIG. 1 is a perspective view of the presently preferred embodiment of a laser catheter assembly in accordance with the present invention.
Figure 3:
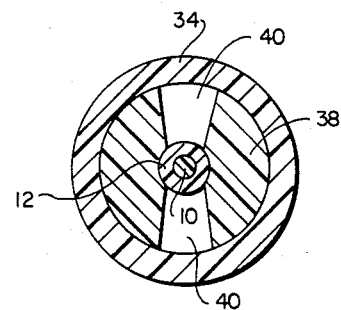
FIG. 3 is a cross-sectional view near the distal end of the laser catheter assembly taken along the line 3—3 of FIG. 2, and drawn to a larger scale.

The present invention is directed to a novel laser catheter assembly incorporating a novel connector for coupling an optical fiber with a laser. Although, for purposes of clarity, the discussion herein will be directed to use of the catheter assembly with an argon laser, it is to be understood that the invention is readily adaptable for use with other lasers.

In the presently preferred embodiment, the optical fiber 10 is a conventional quartz fiber having a bend radius of about two centimeters. This fiber, preferably having a diameter of about 600 microns, is fixed within a silicone cladding 12 that serves as both a mechanical support and as a protective barrier for the otherwise brittle and easily damaged fiber 10. The composite structure of optical fiber and cladding, known as a "dressed optical fiber", is readily available from a number of commercial sources. The presently preferred dressed optical fiber has an outside diameter of 0.043 inches. Of course, many other sizes, types and configurations of optical fibers may be used in connection with the apparatus of the invention without departing from the inventive concept disclosed and claimed herein.

Generally, a beam of laser light emitted from a laser is of a larger diameter than that of optical fiber 10. If the laser beam should strike cladding 12, the cladding will generally be vaporized, the vapor of which tends to collect on and obscure the tip of fiber 10, thus reducing transmission into the fiber, and also increasing the temperature at the end of the fiber due to light absorption.

To solve this problem, a lens system (not shown) is generally incorporated into the laser at a position between the fiber and the source of the laser beam so as to focus the laser beam onto the tip of the fiber. A further protection is obtained by removing cladding 12 from around fiber 10 near the tip thereof, as shown at 10a in FIG. 2.

In the past, it has been thought necessary to construct connectors for interconnecting an optical fiber with a laser beam out of very carefully machined metal components. As noted above, conventional connectors have consisted of many individual pieces, each of which had to be manufactured to extremely fine tolerances in order to fit together properly. This has resulted in high manufacturing costs and significant risk to surgical patients from contamination and from introduction of foreign material from the connector into the patient's body.

Contrary to the conventional approach, it has been found that a unitary connector constructed out of polypropylene, nylon, or similar material by an inexpensive molding process, is as effective as conventional connectors, yet avoids these disadvantages.

The presently preferred embodiment of such a connector 14 includes a coupler portion advantageously consisting of a male fitting member 16 at the proximal end of the connector that is configurated so as to be securely yet slidingly engageable with a corresponding female fitting (not shown) forming part of the laser apparatus. Of course, it will be appreciated that fitting member 16 could be a female fitting with the laser being provided with an appropriate male fitting. It will also be appreciated that other configurations of the coupler portion of the connector may be used in keeping with the general function of securing the optical fiber in proper alignment with laser radiation emitted from a laser. Additionally, although the presently preferred embodiment of the connector is adapted so as to remain secured to the laser by friction-fit of the male member of the connector within the female member of the laser, it would be possible to utilize other methods for securement.

The proximal end of male member 16 is preferably chamfered, as shown at 18, to facilitate insertion. The length of male member 16 should be such that the connector will be securely held and properly aligned with the female fitting when fully inserted. An annular collar 20 may be advantageously provided to establish a positive indication of when the coupler portion of the connector has been completely inserted into the laser, thus assuring optimum placement of the proximal end of the optical fiber within the focused portion of the laser beam.

The proximal end of the presently preferred embodiment of the connector is provided with an axial bore 22 having a diameter about the same or slightly larger than that of the dressed optical fiber, the fiber being permanently secured into position within bore 22, such as by use of an adhesive. When using a dressed optical fiber having an outside diameter of 0.043 inches, it has been found satisfactory to form bore 22 with a diameter of 0.045 inches.

As mentioned above, the cladding is preferably removed from the end portion of fiber 10, as at 10a, and the proximal tip of the fiber is advantageously disposed within a cylindrical cavity 24 so that the laser beam will be somewhat attenuated by being out of focus in the event it becomes misaligned with the optical fiber and strikes the cladding or the end of the connector. The tip of the fiber is preferably recessed slightly within cavity 24 so that it will not be damaged during storage or handling. In the presently preferred embodiment, the tip of the fiber is recessed 0.015 inches.

As mentioned above, it is presently preferred that the diameter of fiber 10 be 600 microns. This is in contrast to conventional catheter assemblies which typically use only a 400 micron fiber. One reason for using the larger fiber is that it is capable of carrying greater amounts of laser energy than smaller fibers. However, another reason is that use of a larger diameter fiber allows for some error in placement of tip 10a within the focused portion of the laser beam (not shown) before any portion of the laser beam will miss the tip of the fiber.

The depth of cylindrical cavity 24 should be shallow enough such that adequate support is given to maintain the tip of fiber 10 in its proper position. If cavity 24 is too deep, the unsupported length of the dressed optical fiber will tend to bend somewhat under the influence of gravity or due to a natural tendency of the fiber to curl, thus resulting in a less than optimum coupling of the laser beam with the optical fiber. At the same time, the depth and diameter of the cavity should be large enough to minimize fouling of the tip of the optical fiber in the event that the focused laser beam is misaligned and the laser beam strikes and vaporizes a portion of the coupler. It would be possible, of course, to insert a reflective disc at the base of cavity 24 to further protect against vaporization of the coupler in the event of misalignment. The presently preferred depth of cavity 24 is 0.090 inches. When the fiber is recessed by 0.015 inches, use of a cavity having a depth of 0.090 inches leaves only 0.075 inches of the fiber unsupported.

It is well known that optical fibers must be cooled during use. Accordingly, the connector is provided with a port 26 near the central portion of the body of the connector that is advantageously adapted for securement to a length of ordinary 0.187 O.D. tubing 28, which in turn is connected to a source of coolant, such as carbon dioxide gas. Port 26 is preferably tapered, as shown, so as to provide a tight connection with tubing 28. It is also advantageous to provide an annular lip 30 at the base of the tapered portion of the port to indicate the position to which the end of tubing 28 should extend when the tubing is properly attached.

In order to provide for proper flow of coolant around the dressed optical fiber, the central portion of the body portion of the connector is advantageously bored out axially to a diameter somewhat greater than that of the dressed optical fiber, as shown at 32. The diameter of central bore 32 in the presently preferred embodiment is 0.080 inches.

In order to provide mechanical protection for the dressed optical fiber and to contain and direct coolant along the length thereof, a length of catheter tubing 34 is disposed about and along the length of the dressed optical fiber and is permanently secured, as by adhesive, into a distal bore 36 advantageously provided at the distal end of the connector. It is preferred that tubing 34 be constructed from polyethylene or similar material, and have inside and outside diameters of 0.077 and 0.095 inches, respectively. Bore 36 is preferably about 0.106 inches in diameter.

The distal end of fiber 10 is held in position within tubing 34 by means of a collet 38, the collet having a plurality of slots 40 that allow passage of coolant past the exposed tip 10b of the optical fiber, and out the end of the catheter assembly. Collet 38 is preferably of molded construction from a material similar to that used in constructing connector 14.

Figure 2:
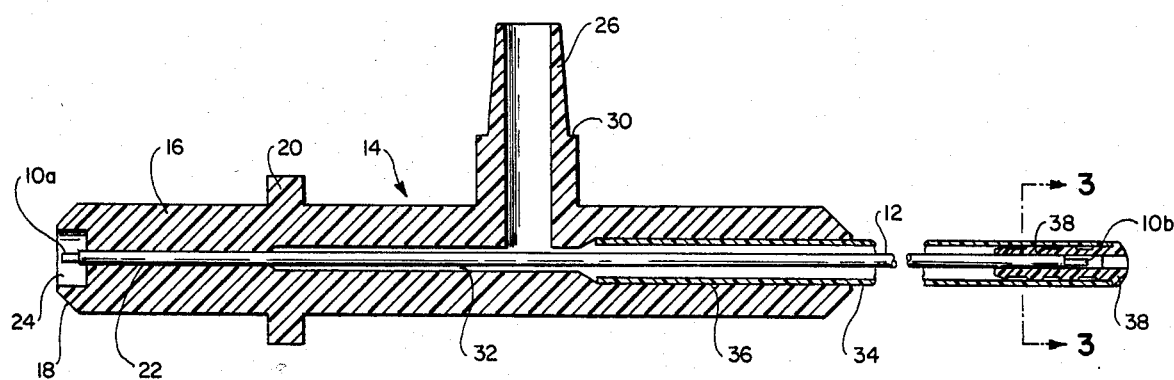
FIG. 2 is a longitudinal section of the laser catheter assembly, taken along line 2—2 of FIG. 1.

As shown in FIG. 2, it is preferred that the distal tip of the optical fiber be recessed within collet 38 for mechanical protection and so that the flow of coolant can aid in preventing the tip of the fiber from being coated with foreign material. If desired, a lens assembly (not shown) may be incorporated into a handpiece and secured to the distal end of the laser catheter assembly so as to permit the laser beam emitted therefrom to be manually focused for use in a particular surgical procedure. However, it has been found that for most applications, no such lens assembly is required, and a surgeon can regulate the diameter and intensity of the emitted beam by adjusting the distance between the distal end of the optical fiber and the tissue being treated.

The particular shape of the novel connector is not critical, and it should be understood that although a basicly cylindrical shape is illustrated in the Figures, a noncylindrical shape may also be utilized within the scope of the present invention. However, use of a cylindrical shape and use of the three stepped-up bores in the manner disclosed above give rise to use of inexpensive molding procedures, whereas some noncylindrical shapes and some other bore configurations would be more difficult to manufacture.

Although the laser catheter may be made in any convenient length, it has been found that a length of about eight feet is adequate for most applications.

From the foregoing, it may be seen that the laser catheter assembly described herein may be easily and inexpensively constructed. For the first time, it is actually possible to economically discard the entire assembly after a single use, thus greatly decreasing the probability of introducing contamination into a surgical site. Use of a disposable laser catheter assembly also results in reduced hospital administrative expenses and a significant decrease in hospital capital expenditures.

Although it was explained above that a lens assembly is generally incorporated into a laser so as to focus the laser beam onto the end of the optical fiber, the laser catheter assembly disclosed herein may also be utilized with lasers lacking such lenses. This may be accomplished by providing an external lens assembly (not shown) adapted for securement to the particular laser, the external lens assembly having a fitting adapted for securement to connector 14. Thus, the lens assembly would be reusable, becoming effectively a portion of the laser apparatus, while the laser catheter assembly could be replaced as often as necessary.

The invention may be embodied in other specific forms without departing from its spirit or essential characteristics. The described embodiment is to be considered in all respects only as illustrative and not restrictive and the scope of the invention is, therefore, indicated by the appended claims rather than by the foregoing description. All claims that come within the meaning and range of equivalency of the claims are to be embraced within their scope.

What is claimed and desired to be secured by a U.S. Letters Patent is:

1. In a laser system having a laser providing in a cylindrical female connector fitting a focused laser beam, apparatus for communicating said beam from its source in said fitting to a medical treatment site, comprising:

(a) an optical fiber assembly, comprising:
  (i) a continuous length of optical fiber of at least 600 microns in diameter extending between a proximal input end and a distal output end;
  (ii) continuous cladding surrounding said fiber between substantially short unclad end portions at the proximal input and distal output ends thereof; and
  (iii) a continuous flexible tube providing a sheath over a major portion of the length of said fiber and cladding;
(b) an integral plastic molded connector having;
  (i) a cylindrical body with one cylindrical end, designated the proximal end, formed to fit within said cylindrical female laser connector fitting with the opposite end of said body being designated as its distal end;
  (ii) an annular collar formed around said body and spaced from its proximal end a first distance corresponding to the proper depth of insertion of said cylindrical body proximal end into said cylindrical female laser connector fitting;
  (iii) a cylindrical open-ended, inwardly-extending cavity formed in said body proximal end concentric with the axis of said body;
  (iv) a first bore concentric with the axis of said body extending from a base portion of said cavity for a second distance substantially equal to the said first distance, said proximal end of said fiber and cladding being snugly fitted and secured within said first bore with the proximal unclad end portion of said fiber extending into said cavity for a third distance less than the depth of said cavity selected to allow said unclad fiber to be self-supporting therein along a fixed axis substantially coinciding with the axis of said first bore;
  (v) a second bore of greater diameter than said first bore forming an extension of said first bore and extending toward the distal end of said body for a fourth distance equal to the length of a selected central portion of said body, said optical fiber and its cladding being loosely mounted therein with said greater diameter providing coolant gas flow space surrounding said optical fiber and cladding;
  (vi) a formed cylindrical tubular port structure concentric with an axis perpendicular to the axis of said body and extending outwardly from said central portion thereof, said port structure forming an outlet communicating with said second bore and adapted for receiving a tubular connection to a source of coolant gas for flowing said gas into said second bore to cool the said optical fiber and cladding mounted therein;
  (vii) a third bore forming a continuation of said second bore and concentric with the axis of said body, said third bore being of greater diameter than said second bore and having a length of the proximal end of said tube sheath secured therein and another portion of said optical fiber and cladding loosely mounted therein whereby coolant gas introduced into said second bore may flow into said third bore and within said tube sheath to cool the remaining portion of said optical fiber and cladding enclosed by said sheath and extending to the distal end thereof; and
(c) an integral plastic molded cylindrical collet secured in the said distal end of said sheath, said collet having a bore extending therethrough and being slotted to permit flow of coolant gas therethrough, the distal end of said optical fiber and cladding being secured in said outlet with the unclad distal end of said optical fiber being mounted and self-supported at a position recessed within the bore of said collet.

* * * * *